United States Patent [19]

Monzyk et al.

[11] Patent Number: 4,882,132

[45] Date of Patent: Nov. 21, 1989

[54] SOLVENT EXTRACTION OF COBALT USING HYDROXAMIC ACIDS

[75] Inventors: Bruce F. Monzyk, Maryland Heights; Arthur R. Henn, Creve Coeur, both of Mo.

[73] Assignee: Monsanto Company, St. Louis, Mo.

[21] Appl. No.: 4,929

[22] Filed: Jan. 20, 1987

Related U.S. Application Data

[63] Continuation of Ser. No. 566,015, Dec. 27, 1983, abandoned.

[51] Int. Cl.$^4$ ................................................ C01G 51/00
[52] U.S. Cl. ........................... 423/139; 423/DIG. 14; 75/101 BE; 75/119; 210/688
[58] Field of Search ........................ 423/139, DIG. 4; 75/101 R, 101 BE, 117; 210/688

[56] References Cited

U.S. PATENT DOCUMENTS

| | | | |
|---|---|---|---|
| 3,224,873 | 12/1965 | Swanson | 75/101 R |
| 3,276,863 | 10/1966 | Drobnick et al. | 75/108 |
| 3,821,351 | 6/1974 | Lucid | 423/9 |
| 4,196,076 | 4/1980 | Fujimoto et al. | 210/21 |
| 4,210,625 | 7/1980 | Flett | 423/139 |
| 4,348,367 | 9/1982 | Rickelton et al. | 423/139 |

OTHER PUBLICATIONS

Chelating Ion—Exchangers Containing N—Substituted Hydroxylamine Functional Groups. Part IV Column Separations on Hydroxomic Acid Resins, Vernon, F., Journal Chin Acta 1976, 83(1), pp. 187-193, Abstracted in Chem. Abs. vol. 85, 1976, 116044B.
A New Mode of Interaction of Carboxylic Acids With N–Phenylbenyohydroxantes of Copper II Cobalt II and Nickel II Bhattacharrya, BC et al., Indian J. Chem., Sect. A 1983, 22A(4) 301-306, Abstracted in Chem. Abs. vol. 99, (1983), 63182(a).
Formation Constants of Metal Chelates of N—M—Toyly—P—Methoxybenzohydroxamic Acid (TMBHA) with some Transition Metals Kasiya KP et al., J. Indian Chem Soc., 1983, 60(20), 189-190, Abstract in Chem. Abs. vol. 98, 1983, 222816h.
Binary Chelates of N—2 Diphenylacetohydroxomic Acid with Cobalt Janardhan, M., et al., Indian J. Chem. Sect. A, 1981, (20), A11, pp. 1136-1137, Abstracted in Chem Abs., vol. 96, 1982, 150,005b.
Vernon "Solvent Extraction of Metals with Hydroxamic Acids", Talanta, vol. 25, pp. 410-412, No. 7, Jul. 1978, (Cl 423/39).
Kirk—Othmer, Encyclopedia of Chemical Technology, Third Edition, vol. 6, pp. 850-851, vol. 9, pp. 713-714.
Vernon et al., Talanta 25 (7), 410-412, (1978).
Vernon et al., Chem. Abstr., 85, 116044b, (1976).

*Primary Examiner*—Robert L. Stoll
*Attorney, Agent, or Firm*—W. W. Brooks; R. H. Shear; A. H. Cole

[57] ABSTRACT

Cobalt is reversibly extracted from cobalt bearing aqueous solutions using solvent extraction techniques by contacting the aqueous solution with a hydrocarbon solvent containing a N-alkylakanohydroxamic acid having at least about 8 carbon atoms. A new class of cobalt complexes is also provided.

13 Claims, No Drawings

SOLVENT EXTRACTION OF COBALT USING HYDROXAMIC ACIDS

This is a continuation, of application Ser. No. 566,015, filed Dec. 27, 1983, now abandoned.

BACKGROUND OF THE INVENTION

The present invention relates to hydrometallury. More particularly, it relates to the extraction of cobalt metal values from aqueous solutions by solvent extraction techniques employing certain N-alkylalkanohydroxamic acids as extractants. Further, it relates cobalt complexes of such alkanohydroxamic acids and organic solutions thereof.

Solvent extraction hydrometallurgy is employed in industrial operations to recover valuable metals. The key to implementing this technology has been the availability of suitable metal extractants. Metal extractants, hereinafter extractants, are organic soluble compounds that form organic soluble complexes with metals which allow the transfer of the metal values from an aqueous solution to an organic phase containing the extractant in contact with the aqueous solution, i.e., extraction, which can be represented generally as follows:

$$M_{aq} + \overline{E} \rightarrow \overline{ME} \tag{1}$$

| $M_{aq}$ = metal in aqueous phase | (A) |
|---|---|
| $\overline{E}$ = extractant in organic phase | (B) |
| $\overline{ME}$ = metal complex in organic phase | (B) |

Unwanted nonmetallic and, depending upon the extractant and conditions employed, metallic impurities are left behind in the aqueous phase (A) which is discarded or further processed for recycle. The metal in the organic phase (B) is then recovered by an aqueous stripping solution phase (C) as follows:

$$\overline{ME} + SS \rightarrow MSS + \overline{E} \tag{2}$$

| SS = aqueous stripping solution phase | (C) |
|---|---|
| MSS = metal in stripping solution phase | (C) |

The method by which stripping is done depends upon the nature of the extraction and the metal involved. By the stripping process (2) the extractant is regenerated and recycled repeatedly in the extraction process. The metal, now concentrated and purified in the aqueous stripping solution phase (C) can be recovered by conventional methods.

Such solvent extraction processes for recovering metal values are known. See, for example, Kirk-Othmer, Encyclopedia of Chemical Technology, Third Edition, Vol. 6 pp. 850–851, Vol. 9. pp. 713–714. U.S. Pat. No. 3,224,873 issued Dec. 21, 1965 to R. R. Swanson discloses a solvent extraction process employing certain oxime extractants for the recovery of copper. U.S. Pat. No. 3,276,863 issued Oct. 4, 1966 to J. L. Drobnick et al discloses the separation of nickel and cobalt values using certain oxime extractants. U.S. Pat. No. 3,821,351 issued June 28, 1974 to M. F. Lucid discloses certain N-substituted hydroxamic acids useful as extractants for the recovery of copper, molybdenum, uranium, iron and vanadium. More recently, efforts have been directed to the extraction of cobalt. For example, U.S. Pat. No. 4,196,076 issued Apr. 1, 1980 to A. Fujimoto et al discloses a method of extracting and separating cobalt from nickel using monoesters of phosphonic acid. U.S. Pat. No. 4,210,625 issued July 1, 1980 to D. S. Flett discloses a method for the separation of cobalt from nickel using an ester of phosphoric acid by solvent extraction. U.S. Pat No. 4,348,367 issued September 7, 1982 to W. A. Rickelton et al discloses a method of extracting cobalt (II) from its aqueous solution using an organic soluble phosphinic acid.

Cobalt is a highly valued metal and aqueous solutions containing cobalt metal values are obtained from processes employed in the hydrometallurgy of ores, the recovery of cobalt and other metals from spent catalysts and the reclaiming of cobalt and other metals from metal scrap. Cobalt occurs in ores that bear nickel, magnesium, copper, lead and zinc.

It is known that cobalt metal values in solution commonly exists as either Co(II) or Co(III) and that these two oxidation states have widely different chemistries when complexed by a ligand. Ligands can be characterized as monodentate which are capable of forming only one bond with the central metal ion and as bidentate which coordinates through two bonds from different parts of the molecule or anion. Co(II) can be converted to Co(III) in the presence of air (oxygen source) depending on the type of ligand used as a metal extractant. Further, it is known that under oxidizing conditions, presence of air, normally Co(II) converts to Co(III) when complexed with a bidentate ligand or chelating agent, i.e., one that bonds to metal ion through at least two atoms thereby, forming a chelate ring complex and that the Co(III) chelate formed is usually irreversible i.e., not readily strippable.

In view of the formation of the Co(III) complexes under aerobic conditions with chelating agents, such agents have not been employed in the solvent extraction of metals from aqueous solutions containing cobalt. Examples of chelating agents known to form irreversible cobalt (III) complexes in the presence of air include the chelating metal extractant used in hydrometallurgy such as the phenolic oximes, available under the tradenames LIX, General Mills, Inc. ACORGA P5000 series, ICI Corporation and SME-529, Shell Chemical, and other known chelating agents, such as ethylenediamine, acetylacetone, oxalic acid, 8-hydroxyquinoline, ethylenediaminetetracetic acid, nitrilotriacetic acid and the like. Accordingly, since monodentate extractants do not form irreversible Co (III) complexes such extractants, for example, derivatives of phosphoric, phosphonic and phosphinic acids, have been developed for the recovery of cobalt in solvent hydrometallurgy.

In view of the much greater activity of chelating agents, such agents are more desirable than monodentate extracts in solvent extraction hydrometallurgy. It has now been discovered that certain N-alkylalkanohydroxamic acid chelating agents reversibly extract cobalt in the presence of air or other oxidizing conditions. This unexpected activity of this class of chelating agents provides an efficient process for extracting cobalt from aqueous solutions containing cobalt by solvent extraction.

Further, this invention provides an effective means to recover cobalt and other valuable metals such as nickel from aqueous feed solutions containing cobalt and nickel metal values.

These and other advantages of the present invention will become apparent from the following description.

SUMMARY OF THE INVENTION

The present invention provides a process for extracting cobalt from cobalt bearing aqueous solutions which comprises contacting said aqueous solution with a hydrocarbon solvent comprising at least 2by weight of N-alkylalkanohydroxamic acid having at least about 8 carbon atoms to extract the cobalt from the aqueous solution; separating the hydrocarbon solvent cobalt loaded organic phase and recovering the cobalt loaded organic phase.

Further, this invention provides a process of extracting cobalt and other metals selected from the group consisting of nickel, zinc, lead, copper and magnesium from aqueous solution containing cobalt and said other metals which comprises contacting said aqueous solution with a hydrocarbon solvent comprising at least 2% by weight of an N-alkylalkanohydroxamic acid having at least about 8 carbon atoms to extract the metals from the aqueous solution; separating the hydrocarbon solvent metal loaded organic phase and recovering the metal loaded organic phase.

The present invention also provides processes, as described above, with the additional steps of contacting the recovered metal loaded organic solution with an aqueous stripping solution to recover the metals from the organic phase; separating the aqueous phase containing the water soluble metal salts; and recovering the stripped organic phase for subsequent reuse in the extraction of another aqueous cobalt-bearing feed solution.

Also, the present invention provides a new class of complexes comprising cobalt and N-alkylalkanohydroxamic acid having at least about 8 carbon atoms and a solubility in a hydrocarbon solvent of at least 2by weight.

DETAILED DESCRIPTION OF THE INVENTION

The N-alkylalkanohydroxamic acids can be employed in accordance with this invention in liquid-liquid extraction processes using columns or mixer-settlers such as the reciprocating-plate extraction column, pulse columns or columns employing rotating impellers and the like.

The N-alkylalkanohydroxamic acid extractant in accordance with this invention are of the type $R_1C(O)N(OH)R_2$ where $R_1$ and $R_2$ are each linear, branched or cyclo aliphatic groups. The useful N-alkylalkanohydroxamic acids have a total of at least about 8 carbon atoms, preferably not more than about 30 carbon atoms, and a solubility of at least 2% by weight in a hydrocarbon solvent and substantially complete insolubility in water (<300 ppm). Aromatic groups and halogens can be present in $R_1$ and $R_2$ provided they do not alter significantly the solubility of the extractant in nonpolar solvents and do not interfere with the chelating ability of the extractant.

It has been discovered that this class of N-alkylalkanohydroxamic acids, which are chelating extractants, reversibly extract cobalt (II) under aerobic conditions. In addition, even if the cobalt is oxidized to the cobalt (III) hydroxamate complex, it still can be easily stripped. This unexpected reversibility provides a process using these chelating extractants for the recovery and purification of cobalt values and other metal values from aqueous streams which also contain cobalt. This is very desirable since chelating extractants are much more selective than monodentate extractants. It opens up a much wider operating pH range and removes the need for complicated monodentate/bidentate synergistic mixtures. Also, it allows cobalt metal values to be more selectively extracted away from gangue minerals, such as $Ca^{2+}$ ion, which would normally co-extract in monodentate extraction systems. Aqueous streams that contain other metal values, such as nickel, zinc, lead, copper and/or magnesium along with cobalt can be processed by these N-alkylalkanohydroxamic chelating extractants since the contained cobalt will not irreversibly complex the extractant.

In addition to the above described hydroxamic compounds the organic phase of the extractant comprises a liquid hydrocarbon solvent. Such solvent must be substantially water immiscible so as to be separable from the aqueous solutions originally containing the cobalt values. Suitable solvents include aliphatic and aromatic hydrocarbons such as kerosene, hexane, toluene, methylene chloride, chloroform, carbon tetrachloride, xylene, naphtha, cyclohexane, Chevron Ion Exchange solvent, Solvesso 100 and the like. Kerosene and other distillates are preferred. Generally, the hydroxamic compounds will be present in the organic phase in an amount of at least about 2% by weight. Preferably, the N-alkyl alkanohydroxamic compound will be present in the amount of 2 to 25%, more preferably about 5 to 20%, by weight based on the total organic phase. Viscosity and/or solubility serves to fix the upper limit of the content of said hydroxamic compound which will depend upon the structure of the compound employed. Normally, an amount of about 15% by weight is employed although amounts as high as 60% can be functional.

The organic phase may also contain modifiers which can be a long chain aliphatic alcohol, such as isodecanol or phosphate esters, such as tributylphosphate. Modifiers serve to prevent third phase formation, aid in phase disengagement and/or increase extractant solubility in the hydrocarbon solvent. If a modifier is used, it can be used in amounts of about 0.5% to 50%, or greater, by volume of the hydrocarbon solvent, preferably about 5%.

In carrying out the process of this invention the cobalt bearing aqueous solution is contacted batchwise or continuously with the extractant solvent comprising at least 2% by weight of the N-alkylalkanohydroxamic acid. The aqueous feed solution bearing cobalt can be adjusted to provide an equilibrium pH in an appropriate range depending upon the particular hydroxamic acid extractant employed. For example, an eqiilibrium pH of at least 5 can be employed for N-methyloctanohydroxamic acid extractant and a pH of at least 7 can be employed for N-isopropyldecanohydroxamic acid. More particularly, an equilibrium pH in the range of 7 to 11 is advantageous employing the N-alkylalkanohydroxamic acid extractants to extract cobalt. Preferably the equilibrium pH for cobalt bearing acidic feed streams is adjusted to a pH in the range of 7 to 8. The volume ratio of the aqueous phase to the organic phase should be selected to most effectively remove the cobalt from the aqueous phase. Aqueous phase to organic phase volume ratios of from 1:20 to 20:2 are believed to be effective, although other ratios may prove effective depending upon the specific characteristics of the solvent extractant and the cobalt bearing aqueous solution employed. Phase contact can be achieved using, for example, mixer-settlers. In the mixer, one phase is dispersed within the other by stirring or some other suitable means of agitation. The extractant forms a complex with the cobalt within the organic phase of the two-phase liquid mixture. The dispersion then flows to the settler where phase disengagement occurs under quiescent conditions. Generally, extraction can be carried out at temperatures in the range of 0° C. to 80° C. or more, preferably in the range 15° to 60° C.

It may be desirable to scrub the cobalt-loaded organic phase to remove co-extracted metal ions to achieve the desired purity depending on the particular cobalt bearing aqueous feed solution employed. This is achieved by washing the cobalt loaded solvent with water or an aqueous solution of a cobalt salt.

The cobalt values extracted from the aqueous feed solution into the organic phase can be stripped from the loaded organic phase by contacting it with about 0.05-10 parts by volume, preferably about 0.5-2.0 parts by volume, of an aqueous solution at 0°-80° C., preferably about 15°-60° C. The aqueous solution used for stripping the loaded organic phase can be a solution of a mineral acid or ammonia. Suitable mineral acids include sulfuric, hydrochloric, hydrofluoric, nitric and the like. The preferred mineral acid solution is sulfuric acid containing about 1-300 grams of sulfuric acid per liter, preferably about 30-100 grams per liter. Suitable aqueous ammonia solutions are solutions containing 50-300 grams ammonia per liter, preferably about 100-200 grams per liter. Phase contact with the stripping solution can be achieved with mixer-settlers, or other suitable devices. In this manner the cobalt is recovered from the organic phase into the stripping solution as a cobalt salt. The cobalt-bearing stripping solution can be treated by conventional means to recover cobalt metal, for example, by hydrogen reduction.

The stripped cobalt-free solvent extractant is recycled to the extraction circuit for treatment of additional aqueous feed solutions bearing cobalt.

In carrying out the present process with aqueous feed solutions containing cobalt and other valuable metals such as nickel, advantage can be taken of the unique property of some of the present extractants to form strippable Co (III) complexes under oxidizing conditions. In this manner the selected extractant will form the cobalt (III) complex along with the other valuable metal complex in the extraction process which enhances preferential stripping of one metal over the other in view of the different stripping characteristics of this cobalt complex and the other metal complex under the selected stripping condition. This provides a means of obtaining very pure cobalt with a minimum number of extraction stripping cycles.

The present invention also relates to the cobalt complexes of the N-alkylalkanohydroxamic acids and to the organic solvent solutions thereof. The term cobalt complex of the N-alkylalkanohydroxamic acid is meant to include compositions of the N-alkylalkanohydroxamic acid having at least about 8 carbon atoms combined with significant amounts of cobalt in either the Co (II) or Co(III) ionic states. Said solutions thereof comprise the hydrocarbon solvent and at least 2% by weight of the cobalt complex of the N-alkylalkanohydroxamic acid. In addition to using these cobalt complexes in the above described processes for recovering cobalt from aqueous leach solutions, these complexes can be used as a source of very pure cobalt for various applications such as the preparation of cobalt catalysts and cobalt supplements for ruminant animals. These cobalt complexes when isolated from the solvent are colored materials in the form of a solid, semi solid, or oily liquid. For example, the N-isopropyldecanohydroxamic acid cobalt coplexes is a dark green oil, the N-methyldecanohydroxamic acid cobalt(III) complex is a dark purplish brown solid and the N-methyldecanohydroxamic acid cobalt(II) complex is a rose colored solid. For convenience of recovery, these complexes were prepared by contacting the hydroxamic extractant in a volatile organic solvent such as methanol, ethanol, petroleum ether and the like with a cobalt source, such as $CoSO_4 7H_2O$, to form the complex and isolating the nonvolatile complex by removing the solvent through evaporation. For example, the N-methyldecanohydroxamic complex was prepared by dissolving 4.02 grams of the hydroxamic acid in 300 ml of methanol in a 500 ml flask fitted with a stirrer. With stirring, 2.81 grams of $CoSO_4 7H_2O$ were added along with 1.68 grams of $NaHCO_3$ to neutralize the hydrogen ions produced when the hydroxamic acid complexes the cobalt. The mixture was stirred about 20 hours, filtered and the methanol was removed from the filtrate by roto-evaporation at 40° C. and drying in a vacuum oven, 12 hours at 30° C., 24 hours at 22° C., to provide a rose colored solid product represented by the formula

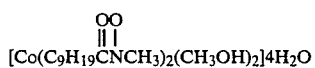

Elemental analysis: Found: Co 9.84; C 48.20; H. 9.01; N 4.88. Calculated: Co 9.89; C 48.39; H 10.15; N 4.70.

The solvent of crystallization can be removed by more vigorous drying conditions.

Methods of preparing the N-alkylalkanohydroxamic acids are known. Such compounds can be prepared by the reaction of a N-alkylhydroxyamine with a carboxylic acid chloride. For example, N-hexyldecanohydroxamic acid is prepared by the dropwise addition of a solution containing 0.064 moles of decanoyl chloride in about 250 ml of methylene chloride to a stirred 2 liter reaction flask charged with 0.064 moles of N-hexylhydroxylamine and 700 ml of methylene chloride maintained at about $-25°$ C. with a dry ice bath. After all the decanoyl chloride is added, 0.04 moles of triethylamine in about 250 ml of methylene chloride is added to remove the HCl by product. The reaction mixtures is quenched with 10 ml of glacial acetic acid and is washed with five 500 ml portions of water. The organic reaction mixture is dried with calcium sulfate and the methylene chloride solvent is removed by rotary evaporation leaving an oily liquid which is allowed to solidify at $-20°$ C. is recrystallized in ethyl acetate and dried to provide N-hexyldecanohydroxamic acid having a melting point of 37° C.

This invention is further illustrated by, but not limited to, the following examples wherein all percentages and parts are by weight unless otherwise indicated.

EXAMPLE 1

This example demonstrates the type of cobalt complexes formed using representative N-alkylalkanohydroxamic acids. A hydrocarbon solution of the N-alkylalkanohydroxamic extractant, about 0.05–0.08 molar concentration, was prepared using a mixture of 95% kerosene and 5% isodecanol (by volume) as the hydrocarbon solvent for each extractant except for the less soluble N-(1-nonyldecyl) cyclohexanohydroxamic acid for which a 50/50 kerosene/isodecanol mixture (by volume) was used. The N-hexylpentanohydroxamic acid extractant solution was prepared at 1.75 molar concentration. An aqueous cobalt (II) nitrate solution was prepared containing 0.1941 g/l (0.003294 M) cobalt (II). Two ml of the aqueous solution were contacted with 2 ml of the organic solution of the extractant by shaking in a test tube. The pH of the mixture was increased to pH 8.5 by adding 3 ml of 0.1 M NaHCO3 solution in increments with vigorous agitation after each addition. The aqueous phase was then analyzed for remaining unextracted cobalt (II). In each case over 98% of the cobalt was extracted. The type of cobalt complexes prepared are shown in Table A.

TABLE A

| EXTRACTANT | COBALT COMPLEX | |
|---|---|---|
| N—ALKYLALKANO-HYDROXAMIC ACID | HA/Co* | Co—OXIDA TION STATE |
| N—methyloctanohydroamic acid | 2/1 | +2 |
| N—methyl-2-ethylhexanohydroxamic acid | 3/1 →2/1** | +3→+2** |
| N—methyldecanohydroxamic acid | 2/1 | +2 |
| N—methylneotridecanohydroxamic acid | 3/1→2/1 | +3→+2 |
| N—methylhexadecanohydroxamic acid | 2/1 | +2 |
| N—hexyldecanohydroxamic acid | 2/1 | +3 |
| N—hexylpentanohydroxamic acid | 2/1 | +3 |
| N—cyclohexyldecanohydroxamic acid | 3/1 | +3 |
| N—isopropyldecanohydroxamic acid | 2/1→3/1 | +3 |
| N—(1-nonyldecyl)cyclohexanohydroxamic acid | 3/1 | +3 |

*HA/Co is the ratio of hydroxamate anions to Co cations, the 2/1 Co(II) complex is pink, the 2/1 Co (III) complex is yellow-brown and the 3/1 Co (III) complex is green.
**Converts on standing as indicated by the symbol→.

The following examples demonstrate the extraction of cobalt from a cobalt bearing aqueous solution and the readily reversible extraction/stripping properties of the cobalt complex formed using the N-alkylalkanohydroxamic acid extractants.

EXAMPLE 2

Ten ml of aqueous 1.94 g/l Co were added to 20 ml water in a 125 ml flask. The pH was 5.03. To this solution was added 10 ml of 10% by weight N-methyloctanohydroxamic acid in kerosene. With mixing, 0.170 ml of 2.5 N NaOH was added to bring the pH to 7.12. During NaOH addition, the organic phase turns pink and the aqueous phase loses its pink color which is indicative of the cobalt being extracted from the aqueous solution into the organic phase by N-methyloctanohydroxamic acid. Analysis of the organic phase showed that 98% of the cobalt had been extracted. Over a 17 minute period the organic phase took on the green color of oxidized cobalt, Co(III). Analysis of the organic phase indicated that all of the cobalt remained in the organic phase. The pH of the aqueous phase was 7.23. Adding 1.0 N H the pH was lowered to 3.76, and the phases were mixed. Analysis showed that 96% of the cobalt returned to the aqueous phase from the organic phase within a few minutes. This illustrates that the cobalt can be stripped rapidly from the organic phase even though it is present as the normally inert Co(III) species. The effect of the presence of an oxidizing agent on the reversibility of the Co(III) species was demonstrated by adjusting the pH to 5.88 with 2.5 N NaOH and adding ten drops of 30% $H_2O_2$ with stirring. The green Co(III) complex formed immediately in the organic phase. The pH of the aqueous phase was lowered to 3.5 using 1 N H with mixing and sample analysis showed that about 55% of the cobalt was quickly stripped from the organic phase and 83% had stripped after a few minutes illustrating that cobalt is readily stripped in the presence of a strong oxidizing agent.

EXAMPLE 3

An aqueous solution was prepared by mixing 10 ml of an aqueous solution containing 1.94 g/l cobalt with 25 ml water containing 0.35 g $KNO_3$. An organic solution was prepared by mixing 1.44 g N-isopropyldecanohydroxamic acid with 25 ml of kerosene containing 5.0 vol. % isodecanol. The aqueous and organic solutions were blended and the pH was increased to 7.92 by slowly adding 1.0 M KOH. The organic phase turned green and remained so on standing for weeks illustrating that the Co (III) complex formation can be permanent. Two 1 ml portions of the cobalt loaded organic phase were taken. One portion was stripped with 5 ml of 120 g/l ammonia solution ($NH_3/NH_4=$)11.5 pH and the other was stripped with 5 ml of dilute sulfuric acid, 1 pH. In each case the cobalt stripped completely over a period of hours demonstrating that even after standing for weeks, the Co(III) can be stripped from the organic phase with stripping solutions having a wide pH range.

EXAMPLE 4

The strippability of representative N-alkylalkanohydroxamic acids were compared using the following procedure. Organic solutions of the HA/Co complex as prepared in Example b 1 were isolated. The organic phase was stripped by blending 2 ml of the organic phase with 2 ml of 0.01 N $H_2SO_4$(pH 2.1) and shaking on a shaker bath at ambient temperature for 10 minutes. The aqueous strip solutions were then analyzed for cobalt. The stripping results using these conditions are set forth in Table B.

TABLE B

| RUN | HYDROXAMIC ACID SOLUTION | % COBALT STRIPPED |
|---|---|---|
| a. | N—methyldecanohydroxamic acid | 77 |
| b. | N—isopropyldecanohydroxamic acid | 56 |
| c. | N—cyclohexyldecanohydroxamic acid | 44 |
| d. | N—(1-nonyldecyl) cyclohexanohydroxamic | 0* |
| e. | N—hexyldecanonhydroxamic acid | 90 |
| f. | N—hexylpentanohydroxamic acid | 80** |
| g. | N—methylneotridecanohydroxamic acid | 63 |
| h. | N—methyl-2-ethylhexanohydroxamic acid | 47 |

*12% stripped using 3 N $H_2SO_4$
**Extractant 1.75 molar concentration

The following examples demonstrate the ability of N-alkylalkanohydroxamic acids to extract cobalt and release, by stripping, the cobalt in the presence of other metals.

EXAMPLE 5

An aqueous solution was prepared by mixing 10 ml of water with 10 ml of an aqueous solution of 1.94 g/l Co and 10 ml of an aqueous solution of 2.14 g/l Ni. The pH of the solution was 5.5. An organic solution was prepared by adding 4.0 g of N-methyldecanohydroxamic acid with 36.0 g of a 95% kerosene/5% isodecanol (V/V) mixture. The aqueous solution and the organic solution were blended at 25° C. The pH of the aqueous phase dropped to about 4.5 after blending and the pH was adjusted slowly with 2.5 N NaOH to 7.77. The organic phase took on the green color of the Co(III) complex. To accelerate oxidation of the cobalt air was passed through the mixture for 15 minutes using a gas dispersion tube. The phases were allowed to separate and analysis indicated that 99.1% of each of the cobalt and nickel had been extracted. The organic phase was isolated and 25 microliters of 30% $H_2O_2$ were added to complete the oxidation of cobalt. The organic phase was stripped by blending with seven 10 ml portions of a pH b 2 buffer solution of 0.M KCl/HCl within about 6 minutes. Analysis showed that 22.6% of the cobalt and b 72.3% of the nickel remained in the organic phase demonstrating that the Co(III) stripped faster than the nickel at the mid stripping condition of pH 2.

The organic phase was then stripped by blending with 10 ml of 300 g/l $H_2SO_4$ (pH about 0) overnight. The green color of Co(III) depleted very rapidly upon contact with this stripping solution. Analysis showed that 99.6% of the total cobalt had been stripped. Also 99.7% of the total nickel was stripped showing utility for recovering nickel in the presence of cobalt which strips more rapidly than the nickel.

EXAMPLE 6

An organic solution and an aqueous solution were prepared in the same manner as Example 5. Ten molar NaOH was added slowly over a 20 minute period to adjust the pH to 7.23. Analysis showed that 99.1% of the cobalt and 99.2% of the nickel had been extracted into the organic phase. To the organic phase was added 0.10 ml of 30% $H_2O_2$ and the solution was mixed thoroughly for one minute. The solution took on the dark green color of Co(III). About 25 ml of an aqueous solution containing 160 g/l $NH_3$ with $NH_3$ $NH_4=2$ (pH 11.5) was added and the phase mixed for about 20 seconds. The phases were allowed to separate. Analysis showed that 90% of the cobalt and 83% of the nickel had been stripped from the organic extractant phase. This demonstrates that cobalt is easily stripped even in the presence of a strong oxidant at high pH and that nickel can be simultaneously recovered.

EXAMPLE 7

N-isopropyldecanohydroxamic acid was dissolved in kerosene containing 5% by volume isodecanol as modifier to provide a concentration of 0.07312 M (16.77 g/l). Twenty ml of this organic solution were contacted with 22 ml of an aqueous solution containing 0.1765 g/l (0.002995 M) of cobalt and 0.1943 g/l (0.003309 M) of nickel as their nitrate salts. The agitated mixture was held at 50° C. and the pH was adjusted slowly to 10.3 with 1.0 M potassium hydroxide fully extracting the cobalt and the organic phase became darker green. After sitting overnight at ambient temperature, the two phases were isolated and the organic phase was stripped by mixing vigorously with 20 ml 0.01N sulfuric acid (pH 2.1) for 5 minutes. The aqueous strip solution was analyzed for both cobalt and nickel; it contained 0.11 g/l of cobalt and 0.16 g/l of nickel. Thus, 67% of the cobalt and 88% of the nickel had been stripped. The organic phase was isolated from the strip solution and washed 3 times with 20 ml of water in a separatory funnel to remove any entrained nickel. A 3 ml aliquot was removed and the organic phase was blended with 20 ml of 0.01 N sulfuric acid stripping solution (pH 2.1) for 30 minutes at ambient temperatures. The aqueous strip solution was analyzed for cobalt and nickel which were found to be present in concentrations of 0 028 g/l cobalt and less than $2\times10^{-6}$ g/l nickel. The purity of the cobalt is greater than 99.99% which is better than analytical reagent grade cobalt. The yield of the pure cobalt was about 18%. Thus, cobalt can be separated from nickel and obtained in better than 99.99% purity by preferentially stripping the nickel from the cobalt and recovering high purity cobalt. To quantify the degree to which the cobalt had been separated from the nickel by the second stripping process a separation factor defined as $$\frac{[Co]_f/[Ni]_f}{[Co]_i/[Ni]_i}$$

(where the subscripts i and f denote the initial an aqueous concentrations, respectively, was determined. The separation factor for this example was 15,420.

EXAMPLE 8

The procedure in Example 7 was repeated with the following modifications. The initial aqueous solution volume was 20 ml. The cobalt and nickel concentrations were 0.1941 g/l and 0.2137 g/l respectively. Concentrated ammonium hydroxide was used to adjust the pH to 10. The organic phase was isolated and stripped with 23.2 ml of 0.01 N sulfuric acid (pH 2.1) for 5 minutes during which air was bubbled through the mixture. After the 5 minute strip, the organic phase was isolated and scrubbed 3 times with 10 ml of 20.751 g/l cobalt (II) aqueous solution containing about 0.03 g/l nickel. The scrubbed organic phase was then stripped at pH 1.2 for 30 minutes with 20 ml of 0.1 N H Analysis of the initial 5 minute strip showed 0.075 g/l of cobalt and 0.137 g/l of nickel or only about 45% of the cobalt was stripped. The concentrations of cobalt and nickel in the final strip solution were 0.197 g/l cobalt and 0.00017 g/l nickel. Some of the cobalt was gained from scrubbing with the concentrated cobalt solution. The yield of cobalt from the initial aqueous solution is about 55%. The separation factor is 1276 and the percent purity of cobalt is 99.91%.

EXAMPLE b 9

An aqueous solution was prepared by mixing 10 ml of water with 10 ml of 1.94 g/l cobalt and 10 ml of 2.14 g/l nickel. This aqueous solution was contacted with 40 ml of an organic solution of 95% kerosene 5% isodecanol (V/V) containing 10% by weight N-methyldecanohydroxamic acid. The mixture was agitated and the pH was adjusted to 7.77 by the addition of 2.5 N NaOH dropwise over a 30 minute period. about 99% of the nickel and the cobalt were extracted into the organic phase. The organic phase was isolated and stripped by blending with Fisher brand pH 2 buffer (0.05 M KCl/HCl) solution and agitated for about 6 minutes. The phases were allowed to separate and upon analysis the organic phase contained 23% of the cobalt and 72% of the nickel illustrating preferential recovery of cobalt in the presence of nickel.

The N-alkyl alkanohydroxamic acid extractants can be employed to separate cobalt from metals other than nickel.

The procedures set forth in the above Examples for separating cobalt from aqueous solutions also containing nickel are also applicable for the separation of cobalt from other metals such as copper, zinc, lead or magnesium.

In view of the foregoing description one skilled in the art of extractive hydrometallurgy techniques can by routine evaluation select the proper N-alkylalkanohydroxamic acid extractant and stripping procedures to recover cobalt from various aqueous feed streams bearing cobalt.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A process for extracting cobalt from a cobalt bearing aqueous solution which comprises:
   (a) contacting the aqueous solution at an equilibrium pH of at least about 7 with a hydrocarbon solvent comprising at least 2% by weight of an N-alkylalkanohydroxamic acid having at least about 8 carbon atoms to extract cobalt from the aqueous solution;
   (b) separating the hydrocarbon solvent cobalt loaded organic phase; and
   (c) recovering the cobalt loaded organic phase.

2. The process of claim 1 wherein the N-alkylalkanohydroxamic acid has no more than about 30 carbon atoms.

3. The process of claim 1 wherein the N-alkylalkanohydroxamic acid has the general formula $R_1C(O)N(OH)R_2$ wherin $R_1$ and $R_2$ are each linear, branched or cyclo aliphatic groups such that said hydroxamic acid has at least about b 8 and not more than about 30 carbon atoms and a solubility of at least 2% by weight in a hydrocarbon solvent.

4. The process of claim 3 wherein $R_2$ is methyl.

5. The process of claim 3 wherein $R_2$ is a branched or cyclo aliphatic group.

6. The process of claim 3 wherein the hydroxamic acid is N-methyloctanohydroxamic acid.

7. The process of claim 3 wherein the hydroxamic acid is N-isopropyldecanohydroxamic acid.

8. The process of claim 1 wherein the hydrocarbon solvent is selected from kerosene and kerosene containing up to 50% by volume of a modifier.

9. The process of claim 1 wherein the cobalt bearing aqueous solution also contains one or more metal values selected from nickel, magnesium, copper, lead or zinc and said metal values are coextracted with the cobalt.

10. The process of claim 9 wherein said metal values are nickel.

11. The process of claim 1 further comprising the steps of: contacting the cobalt loaded organic phase with an aqueous stripping solution to strip the cobalt into the aqueous phase; separating the cobalt containing aqueous phase; and recovering the stripped organic phase for subsequent reuse.

12. The process of claim 1 wherein the equilibrium pH is from about 7 to about 11.

13. The process of claim 12 wherein the equilibrium pH is from about 7 to about 8.

* * * * *

UNITED STATES PATENT AND TRADEMARK OFFICE
CERTIFICATE OF CORRECTION

PATENT NO. : 4,882,132

DATED : November 21, 1989

INVENTOR(S) : B. F. Monzyk et al

It is certified that error appears in the above-identified patent and that said Letters Patent is hereby corrected as shown below:

Title page:

In the Abstract, 4th line, delete "N-alkylakanohydroxamic" and insert therefor --N-alkylalkanohydroxamic--.

In Column 1, line 26, delete "tm".

In Column 3, line 6, delete "2by" and insert therefor --2% by--.

In Column 3, line 35, delete "2by" and insert therefor --2% by--.

In Column 4, line 51, delete "eqiilibrium" and insert therefor --equilibrium--.

In Column 4, line 63, delete "20:2" and insert therefor --20:1--.

In Column 7, line 62, delete "1.0 N H" and insert therefor --1.0 N $H_2SO_4$--.

In Column 8, line 6, delete "1 N H" and insert therefor --1 N $H_2SO_4$--.

In Column 8, line 25, after "=" insert "2".

In Column 8, line 36, delete "b" after the word "Example".

In Column 9, line 14, delete "b" after the word "pH".

UNITED STATES PATENT AND TRADEMARK OFFICE
CERTIFICATE OF CORRECTION

PATENT NO. : 4,882,132

DATED : November 21, 1989

INVENTOR(S) : B. F. Monzyk et al

It is certified that error appears in the above-identified patent and that said Letters Patent is hereby corrected as shown below:

In Column 9, line 14, delete "0.M" and insert therefor --0.1M--.

In Column 9, line 16, delete "b" at the beginning of the line.

In Column 9, line 18, delete "mid" and insert therefor --mild--.

In Column 9, line 38, delete "$NH_3\ NH_4$" and insert therefor --$NH_3/NH_4$--.

In Column 10, line 19, delete "an" and insert therefor --and final--.

In Column 10, line 36, delete "H" and insert therefor "$H_2SO_4$"--.

In Column 10, line 46, delete "b" after the word "Example".

In Column 10, line 55, delete "about" and insert therefor --About--.

UNITED STATES PATENT AND TRADEMARK OFFICE
CERTIFICATE OF CORRECTION

PATENT NO. : 4,882,132

DATED : November 21, 1989

INVENTOR(S) : B. F. Monzyk, et al

It is certified that error appears in the above-identified patent and that said Letters Patent is hereby corrected as shown below:

In column 12, line 5, delete "b" after the word "about".

Signed and Sealed this

Sixth Day of November, 1990

Attest:

HARRY F. MANBECK, JR.

Attesting Officer

Commissioner of Patents and Trademarks